(12) United States Patent
Hahn

(10) Patent No.: US 9,314,271 B2
(45) Date of Patent: Apr. 19, 2016

(54) DEVICE FOR STRETCHING SKIN

(71) Applicant: Karl Storz GmbH & Co. KG, Tuttlingen (DE)

(72) Inventor: Martin Hahn, Altheim (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 558 days.

(21) Appl. No.: 13/624,629

(22) Filed: Sep. 21, 2012

(65) Prior Publication Data

US 2013/0079821 A1   Mar. 28, 2013

(30) Foreign Application Priority Data

Sep. 23, 2011   (DE) .......................... 10 2011 114 374

(51) Int. Cl.
| | | |
|---|---|---|
| *A61B 17/42* | (2006.01) | |
| *A61B 17/04* | (2006.01) | |
| *A61B 19/00* | (2006.01) | |

(52) U.S. Cl.
CPC ................. *A61B 17/42* (2013.01); *A61B 17/04* (2013.01); *A61B 19/24* (2013.01); *A61B 2017/0496* (2013.01)

(58) Field of Classification Search
CPC ............. A61B 17/042; A61B 17/0466; A61B 2017/081; A61B 2017/086; A61B 2017/088; A61B 2017/0496; A61B 19/24; A61B 17/42
USPC .......... 606/103, 148, 215, 216, 217, 232, 233
See application file for complete search history.

(56) References Cited

U.S. PATENT DOCUMENTS

| | | | |
|---|---|---|---|
| 3,650,274 A | 3/1972 | Edwards et al. | |
| 6,471,715 B1 | 10/2002 | Weiss | |
| 2003/0009178 A1* | 1/2003 | Fields et al. | .................. 606/132 |
| 2006/0058842 A1 | 3/2006 | Wilke et al. | |
| 2006/0229676 A1 | 10/2006 | Doll et al. | |
| 2009/0018579 A1 | 1/2009 | Wilke et al. | |

FOREIGN PATENT DOCUMENTS

| | | |
|---|---|---|
| DE | 10349953 B4 | 6/2006 |
| EP | 2279701 A1 | 2/2011 |
| FR | 2928258 A1 | 9/2009 |
| RU | 2207812 C2 | 7/2003 |
| WO | 2009118487 A1 | 10/2009 |

OTHER PUBLICATIONS

European Search Report Application No. 12 18 5261 Completed: May 18, 2015; Mailing Date: May 28, 2015 5 pages.

* cited by examiner

*Primary Examiner* — Kathleen Holwerda
*Assistant Examiner* — Kankindi Rwego
(74) *Attorney, Agent, or Firm* — Whitmyer IP Group LLC

(57) ABSTRACT

A device for stretching skin having a plate-shaped main body and a tensioning element thereon. The tensioning element is rotatable about an axis of rotation, as a result of which a pulling thread affixed to the tensioning element is able to be wound up. A latching lock serves for fixing the rotatable tensioning element and includes a securing device for securing the latching lock against inadvertent release. The tensioning element is able to be moved in a direction of the axis of rotation against a force of a spring. The latching lock is able to be removed from a latching position, and return to the latching position as a result of a force from the spring. The securing is able to be actioned by a securing lever arranged on the rotatable tensioning element. A movement of the securing lever is able to action the tensioning element at the same time.

14 Claims, 6 Drawing Sheets

DEVICE FOR STRETCHING SKIN

BACKGROUND OF THE INVENTION

The invention relates to a device for stretching skin.

Such a device is known from DE 103 49 953 B4. This device serves for fixing and tensioning at least one pulling thread for constructing a neovagina. Constructing a neovagina is understood to mean a vaginal reconstruction, which is performed in the absence of a vaginal structure, the latter being a malformation of the female genitalia, as seen in Mayer-Rokitansky-Küster syndrome and in cases of testicular feminization.

The surgical principle involved in constructing a neovagina lies in stretching the vaginal dimple. A plastic olive or phantom, which is connected to two pulling threads, is used to apply continuous pressure on the vaginal dimple. As a result, this region of skin is stretched and a neovagina is formed within days. Here the pulling threads are wound onto a tensioning element of the device for stretching skin. Within the scope of the procedure of constructing the neovagina, frequent re-tensioning of the pulling threads is required because the plastic olive or the phantom exerts continuous pressure on the vaginal dimple and the latter should stretch in the process. A latching lock serves to hold the tensioning element in a specific rotational position for tensioning the thread; to be precise until the skin has correspondingly stretched. The tensioning element is once again turned thereafter in order again to build up additional tension in the thread. The latching lock has an actuation element arranged laterally next to the tensioning element, by means of which actuation element a first blocking element can be made to engage with a toothed wheel for blocking purposes or by means of which the latching lock can be lifted by lateral away movement from the tensioning element. In order to secure against inadvertent movement of the actuation element, a second displaceable actuation element is arranged, which is arranged even further away from the tensioning element and can introduce a second blocking element into the movement path of the first blocking element; to be precise, into the displacement path thereof such that this first blocking element is thereafter blocked against inadvertent release.

In dermal surgery, particularly in plastic-reconstructive surgery, it is necessary to stretch the skin on both sides of lesions prior to removing the lesion. The exscinding or removing of lesions includes, inter alia, the removal of skin tumours, birth marks or large-area scars.

To this end, a plate-shaped main body is placed onto the skin on both sides of the lesion and these two main bodies are interconnected by means of pulling threads which are routed subcutaneously.

On at least one of the two main bodies there is a tensioning element, onto which the pulling thread or threads can be wound and tensioned. As a result, the two plate-shaped main bodies successively approach one another and arc the tissue, e.g. a scar, present between the two successively approaching plate-shaped main bodies upwards. The region of skin that should be stretched is the respective region of skin "behind" the plates approaching one another.

In the process it is necessary, if need be over a period of a plurality of weeks, to permanently tension and re-tension the pulling threads.

It should be possible for this re-tensioning to be performed by the patient in a simple and safe manner, particularly so that there is no need to visit a medical practitioner within the scope of outpatient treatment for each individual tensioning process.

Overall, the device should have such a design that even persons with little technical knowledge can perform the tensioning process by simple manipulation.

It is therefore an object of the present invention to provide a device of the type mentioned at the outset to the extent that such a tensioning process can be performed simply and safely using a design that is as simple as possible.

SUMMARY OF THE INVENTION

According to the invention, the object is achieved by a device for stretching skin, comprising a plate-shaped main body, a tensioning element arranged on said main body, said tensioning element being rotatable about an axis of rotation, as a result of which a pulling thread affixed on said tensioning element can be wound up on said tensioning element and tensioned, a latching lock for fixing said rotatable tensioning element, said latching lock comprising a securing for securing said latching lock against inadvertent release, wherein said tensioning element can be moved in a direction of said axis of rotation against a force of a spring, as a result of which said latching lock can be removed from a latching position, and when said tensioning element is released the latter can be returned to said latching position as a result of said force from said spring, and wherein said securing can be actioned by a securing lever arranged on said rotatable tensioning element, by means of which securing lever a movement of said tensioning element can be actioned at a same time.

From a design point of view, these measures have the significant advantage that all components required for the manipulation are arranged directly on the tensioning element. During the manipulation as such it is only necessary to actuate a single operating element, namely the securing lever. It is possible to move the tensioning element against the force from the spring by means of this securing lever, with the latching lock being unlatched in the process. Then, for the purpose of tensioning, the tensioning element can be turned by means of the securing lever. As a result of releasing or reducing the force acting on the spring, the latter autonomously presses the tensioning element back into the latching position. At the same time, this securing lever is also the actuation element by means of which the securing against inadvertent movement of the tensioning element is actioned.

Manipulation is therefore very simple and safe for the patient because he/she only has to grasp and operate a single element, namely the securing lever. Moving the tensioning element against the force from the spring, i.e. either pressing in or pulling off, is a simple process. Free rotatability sets in thereafter. When the tensioning element is released, the spring in automatic fashion immediately presses the latching lock back into the blocking position. For the purpose of securing, only one further manipulation needs to be performed with the securing lever in order to secure the tensioning element against inadvertent actuation.

This significantly simplifies the handling for the patient and provides a device with a compact design because all components are realized on the tensioning element itself.

In a further embodiment, the securing lever does not secure in a first position raised from the tensioning element and can be brought into a second, pivoted down position, in which it blocks a movement of the tensioning element in the direction of the axis of rotation.

An advantage of this measure is that, in the raised position, the securing lever can be grasped by the operating person in an ergonomic fashion in order to move the tensioning element, i.e. move it along the axis of rotation against the force from the spring and subsequently turn it in order to tension the thread.

As a result of a transition into the second pivoted-down position, the securing lever no longer projects outwards, and therefore it does not project from the body of the patient either, such that said patient can, for example, wear a piece of clothing over said securing lever without it being possible to identify that such a device for stretching skin has been affixed to the body. In this pivoted down position the securing lever then satisfies its securing function, i.e. it blocks every movement of the tensioning element.

In a further embodiment of the invention, the securing lever can be pivoted about a lever axis which runs perpendicularly to the axis of rotation of the tensioning element.

An advantage of this measure is that in this axis alignment the securing lever is raised from the tensioning element in one position and can therefore be easily grasped. By pivoting down, the securing lever then rests on the tensioning element and requires little installation space.

In a further embodiment of the invention, the securing lever rests on a securing pin, extending along the axis of rotation, via a cam, said securing pin allowing a movement of the tensioning element along the axis of rotation in the first, raised position of the securing lever but blocking said movement in the second, pivoted down position.

An advantage of this measure is that during the pivoting down of the securing lever via the cam the securing pin is necessarily brought into a position which blocks a movement of the tensioning element, and so the securing function is satisfied.

In a further embodiment of the invention, the securing lever can, from the second pivoted down position, be displaced into a further position which prevents the securing lever from pivoting upwards.

Additional securing is obtained by this measure.

Although the tensioning element is already secured against movement by pivoting down the securing lever, the securing lever itself, for example in the case of a clumsy body movement or in the case of body contact with another person, can inadvertently be pivoted upwards, as a result of which the securing would then be lifted.

As a result of displacing the securing lever into the further position, the latter itself is now even blocked against being pivoted upwards, and hence it is secured.

In order to lift this double securing, the securing lever must initially be displaced from the further position and it can only then be pivoted upwards.

According to the basic principle of the invention, this can be actioned using a single component using a single hand, and so the simple manipulation is not adversely affected by this additional double securing measure either.

In a further embodiment of the invention, the cam has a rounded cam surface facing the securing pin, said cam surface actioning an axial displacement of the securing pin when the securing lever is pivoted over.

An advantage of this measure is that the conversion of the pivoting down or raising movement of the securing lever via the cam into a linear displacement of the securing pin is actioned in a smooth and targeted manner.

In a further embodiment of the invention, the securing lever has at least one slot, in which at least one axle pin extending along the lever axis is held, wherein, in the second, pivoted down position of the securing lever, the latter can be swung about the axle pin whereas this swing movement is blocked in a further laterally displaced position of the securing lever.

An advantage of this measure is that this second stage of securing is achieved by mechanically simple and robust means. For the handling person, this means that the securing lever merely needs to be displaced from this position, wherein the axle pin runs in the slot, to be precise until it has reached a position at the end of the slot from where the securing lever can then be pivoted upwards again. The handling person feels this; for example, if the securing lever has not been displaced far enough in the lateral direction, it simply cannot be pivoted upwards. This only is possible once the axle pin has reached an end position in the slot. Hence the handling person need not perform this displacement movement under visual monitoring; rather, it is possible to determine by tactile means when the axle pin butts against an end of the slot.

In a further embodiment of the invention, the tensioning element is held in a cut-out in the main body, wherein the axis of rotation of the tensioning element stands up from the main body and the tensioning element can be moved towards the main body against the force from the spring.

This measure has a number of advantages from a design and handling point of view. First of all, the tensioning element is not raised unnecessarily high and far away from the main body but rather it is, at least in part, held in the cut-out in the main body. The patient has affixed the plate-shaped main body on his/her body via the pulling threads, for example in the abdominal region or on an upper thigh. From the patient's point of view, it is ergonomic, when the securing lever is pivoted upwards, to press the tensioning element further into the main body against the force from the spring and then bring about the rotation. The plate-shaped main body, affixed to the skin of the patient via the pulling threads, provides the sufficient resistance force in order to press in the tensioning element against the force from the spring. From a design point of view, this spring can then be arranged between the main body and the tensioning element and said spring is accordingly tensioned when the tensioning element is pressed into the main body. After the release, said spring then presses the tensioning element away from the main body to such an extent that the latching lock is situated in the latching position.

In a further embodiment of the invention, the latching lock has at least one latch protruding into the cut-out in the main body, which latch, in the latching position, is in blocking engagement with a toothed wheel of the tensioning element.

The advantage of this measure is that such a latch can be embodied in a relatively stable fashion and can also be fixedly connected to the main body, for example by virtue of being welded into the cut-out. In the "normal position", this latch is in blocking engagement with the toothed wheel of the tensioning element. The tensioning element is brought out of this blocking engagement in a very simple fashion by virtue of the fact that it is moved in the direction of the axis of rotation against the force from the spring. After this, the effect of the latching lock is lifted and the tensioning element can be turned to wind up and tension the thread, if the tensioning element is released, the spring once again presses the toothed wheel of the tensioning element into blocking engagement with the latch.

In a further embodiment of the invention, the at least one latch and/or the teeth of the toothed wheel are chamfered at the flanks thereof.

An advantage of this measure is that this automatic latching movement results in a secure blocking engagement and that a tooth of the toothed wheel, if it falls precisely on the latch, would not block further axial movement. As a result of the chamfers, the toothed wheel rotates at least so far relative to the spatially fixed latch that the latch can enter between two teeth.

In a further embodiment of the invention, the tensioning element has a reel body, onto which the at least one pulling thread can be wound, and the pivotable securing lever is assembled on the end of the reel body facing away from the main body.

From a design point of view, this measure is in turn advantageous in that simple elements with a compact design make it possible to bring about winding up and also tensioning of the thread by the reel body, controlling the tensioning element between the various positions by means of the securing lever and, ultimately, the securing in a simple manner.

In a further embodiment of the invention, the securing lever is embodied as a plane element, which comes to rest on the upper end of the reel body in the pivoted-down state.

The embodiment as a plane element provides the handling person with a sufficiently large areal piece which can, for example, be grasped between the thumb and the index finger. After being pivoted down, the areal element nestles against the upper side of the reel body and does not constitute an unnecessarily raised component.

If such a device is affixed e.g. in the region of the chest or the abdomen of a patient, the latter can wear pieces of clothing over the device without there being a risk of said clothing becoming entangled with projecting awkwardly shaped components. At the same time, one cannot immediately identify that the person is carrying such a device in a fixed fashion, which is very beneficial to patient compliance.

In a further embodiment of the invention, two flaps protrude from the plane element, in which flaps slots have been cut out, and one axle pin extending along the lever axis is respectively held in the slots.

An advantage of this measure is that simple design means affords the possibility of a fixed connection between the securing lever and the tensioning element and that, at the same time, the movement for pivoting the securing lever upwards and downwards is provided as is, after shifting, the lateral displaceability.

In a further embodiment of the invention, the flaps are embodied such that these project on one side of the lever axis and rest against the reel body in the case of a pivoted-down and laterally displaced securing lever, as a result of which the securing lever is prevented from pivoting upwards.

A significant advantage of this measure is that, by resting against and projecting beyond the lever axis opposite to the areal element, these flaps ensure that the securing lever can no longer be pivoted upwards in this displaced state.

In a further embodiment of the invention, the flaps extend away from the areal element in the plane of the latter.

An advantage of this measure is that, in the case of a pivoted-over and laterally displaced securing lever, the components thereof all lie in a plane and can nestle tightly against a correspondingly designed surface of the tensioning element.

It is understood that the features mentioned above and the features yet to be explained below can be used not only in the respectively specified combination but also in other combinations or on their own, without departing from the scope of the present invention.

On the basis of a selected exemplary embodiment, the invention will be explained and described in more detail below in conjunction with the attached drawings, in which:

DESCRIPTION OF PREFERRED EMBODIMENTS

Figure 1:
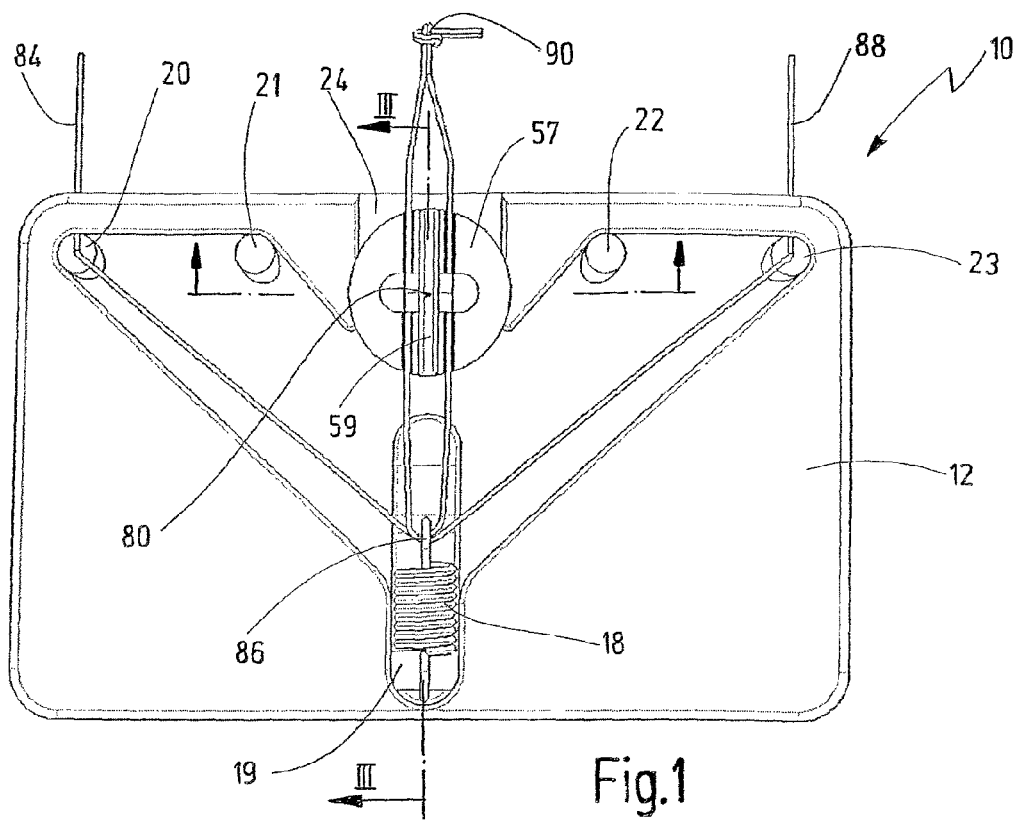
FIG. 1 shows a plan view of a device for stretching skin, wherein the guidance of two pulling threads is illustrated.

An exemplary embodiment of a device according to the invention, illustrated in FIGS. 1 to 12, for stretching skin is denoted by reference sign 10 in its entirety. Initially, the structural components of the device 10 will be described in conjunction with FIGS. 1 to 6. The device 10 has a plate-shaped main body 12, which, in the illustrated exemplary embodiment, consists of a rectangular planar plate 14 of medical steel or skin-friendly polymeric material. By way of example, the plate 14 has dimensions of 8×5 cm. A roughly triangular recess 16 has been cut out of one side of the plate 14. A tensioning spring 18 has been inserted into the region of the tip of the roughly triangular recess 16 and it is anchored in the plate-shaped main body 12 via a rod 19. An end of the tensioning spring 18 facing the recess 16 has an ear 86 through which pulling threads 84 and 88 can be routed, as will still be explained later.

In the region of the longer rectangular side lying opposite the tensioning spring 18 there are four bores 20, 21, 22, 23, which pass through the plate 14.

These bores 20 to 23 serve for affording the possibility of routing pulling threads 84, 88 through the plate 14.

In region between the bores 21 and 22 there is a cut-out 24 in the plate 14 (see also FIG. 3) in which a tensioning element 26 has been assembled.

The tensioning element 26 has a reel body 28 with an approximately circular cross section, which has an encircling circumferential notch 30. A sleeve 32 is screwed into the lower end of the reel body 28.

The sleeve 32 has a raised cylindrical section 34, which reaches into a cut-out 36 in the lower region of the reel body 28 and is fixedly screwed to the reel body 28 by appropriate male/female threads.

Figure 5:
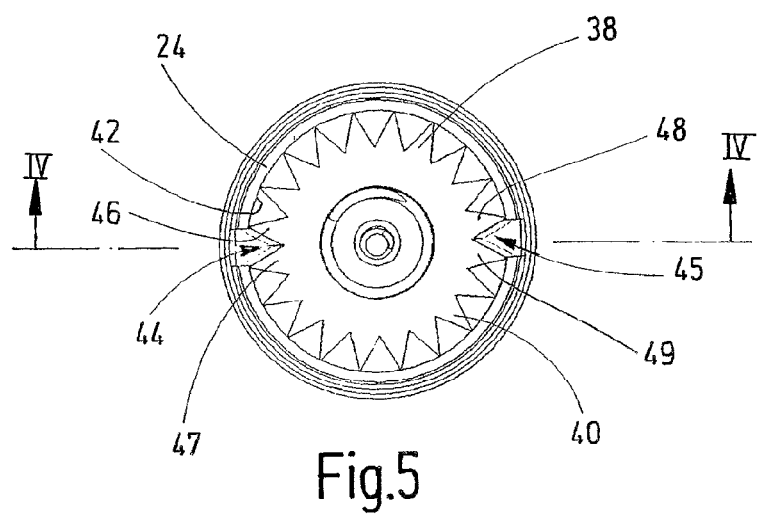
FIG. 5 shows a section along the line V-V in FIG. 4, level with the latching lock.

At its lower end, the sleeve 32 has an annular flange 38 which is embodied as toothed wheel 40, as is possible to identify from FIG. 5 in particular.

Protruding diametrically opposite to one another from the inner wall 42 of the recess 36 there are two latches 44 and 45, which are fixedly welded to the inner wall 42.

The latches 44 and 45 are designed and arranged at such a level that they can enter into blocking engagement with teeth 46, 47, 48 and 49 of the toothed wheel 40. The tensioning element 26 is held in the cut-out 36 by a holding ring 50 such that it cannot be lost.

The latches 44 and 45 as well as the toothed wheel 40 with the teeth 46 to 49 thereof form a latching lock 51. In the position illustrated in FIGS. 1 to 5, which is referred to as "normal position" of the tensioning element 26, the latching lock 51 blocks a rotation of the tensioning element 26 about the axis of rotation 80 thereof. Held in the interior of the sleeve 32 there is a first spring 52, which is supported firstly on the base 53 of the recess 24 and, opposite thereto, on the corresponding base in the cut-out 36 in the reel body 28. The first spring 52 is configured such that, when no force acts thereon, it keeps the tensioning element 26 in this normal position.

Provided passing centrally through the reel body 28 there is a securing pin 54, at the lower end of which a blind hole 56 is present which holds a second spring 55.

In the region of the cut-out 36 in the reel body 28, this securing pin 54 is encircled by the first spring 52. The second spring 55 in turn is supported firstly on the base 53 of the recess 24 and on the base of the blind hole 56. A cam 74 of a securing lever 59 rests on the upper end 76 of the securing pin 54. As is possible to identify, particularly from the perspective illustrations and from the sectional illustration from FIG. 3, the securing lever 59 is embodied as a plane element 61, approximately in the shape of a semi-circular disc, with two flaps 63 and 64 extending away therefrom in the plane of extent thereof.

A slot 65 and 66, respectively, is present in each of the flaps 63 and 64.

The securing lever 59 is assembled on the upper side of the reel body 28 via two axle pins 68 and 69, which pass through the slots 65 and 66. Here, the axle pins 68 and 69 are held in corresponding bearing blocks 70 and 71 as well as 72 and 73 arranged on both sides of the flaps 63 and 64.

In FIGS. 1 to 4, the securing lever 59 is illustrated in its raised or pivoted-upwards position. It is possible, particularly in the sectional illustrations of FIGS. 3 and 4, to identify that the underside of the tensioning element 26 is at a distance from the base 53 of the cut-out 24 in the normal position that can be seen therein.

The whole assemblage of reel body 28, sleeve 32, securing pin 54 and securing lever 59 can be displaced along the axis of rotation 80 in the direction of the base 53 of the cut-out 24 against the force from the first spring 52.

To this end, the pivoted-upwards securing lever 59 can be grasped between a thumb and an index finger and the assemblage can be pressed in by manual force.

Figure 6:
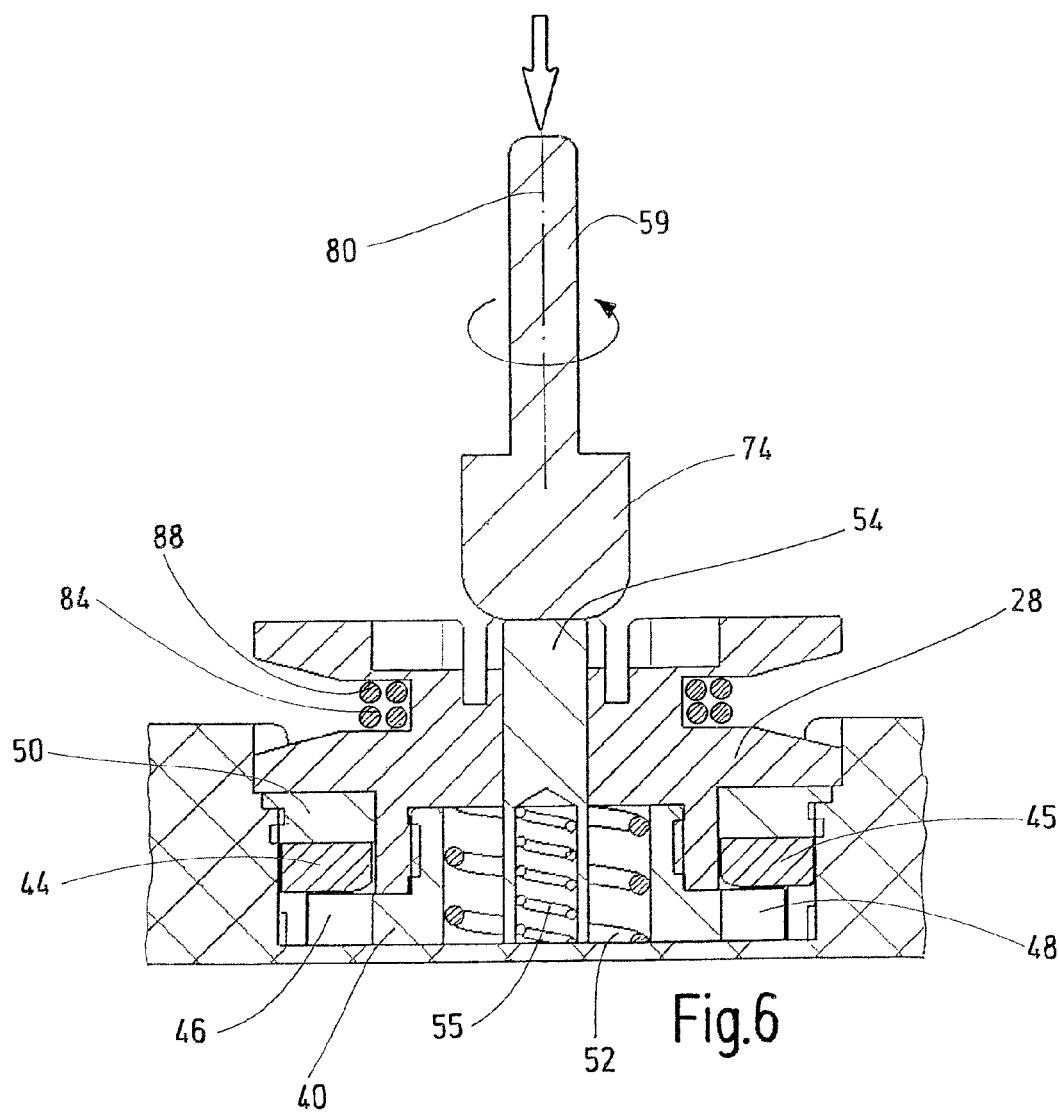
FIG. 6 shows the section of FIG. 4 with tensioning element pressed into the main body against the force from the spring.

This situation is illustrated in FIG. 6. From the sectional illustration, it is now possible to identify that the tensioning element 26, and hence the toothed wheel 40 as well, has been moved that far down, i.e. pressed into the cut-out 24, that the teeth 46 and 48 (one can see the flanks thereof in the sectional illustration of FIG. 6) have left the blocking engagement with the spatially fixed latches 44 and 45.

The reel body 28 can now be rotated freely and it is possible to wind pulling threads 84 and 88 onto the reel body 28 by turning the tensioning element 26.

Figure 2:
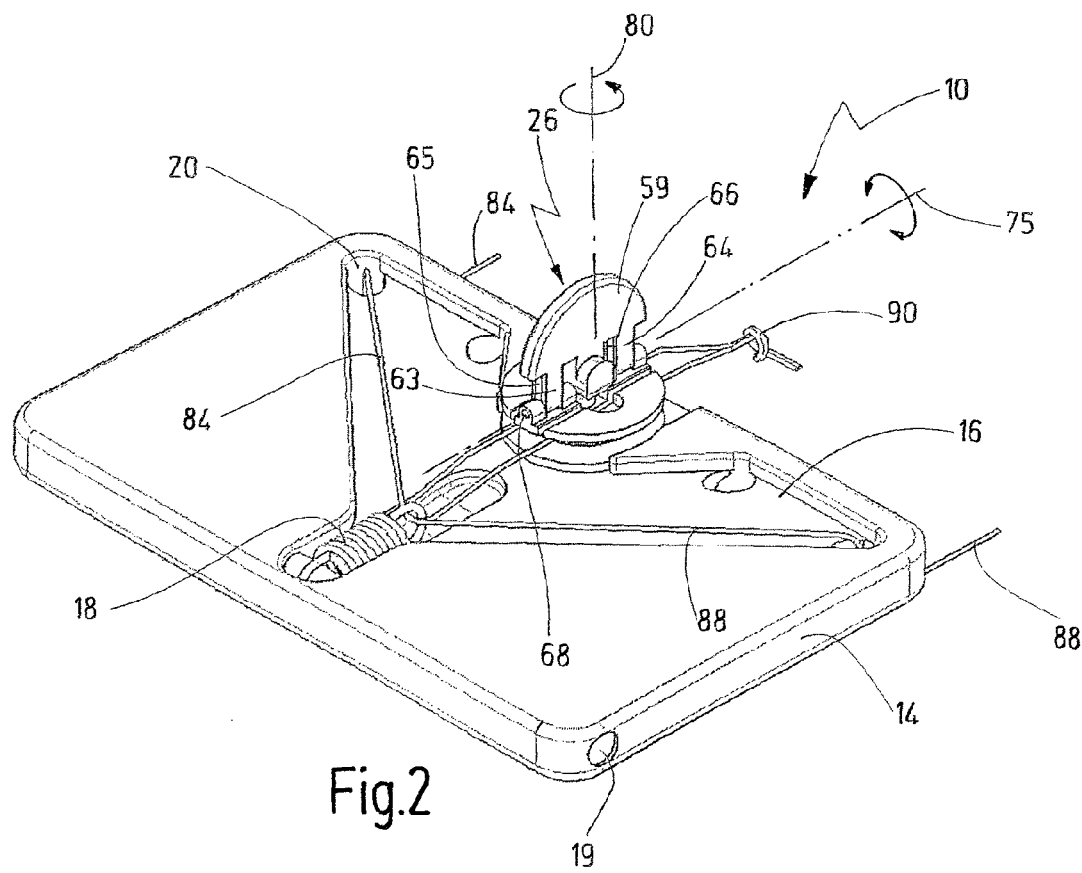
FIG. 2 shows a perspective view of the device from FIG. 1.

An example of routing such pulling threads 84 and 88 is illustrated in FIGS. 1 and 2. A first pulling thread 84 is routed towards the underside of the plate 14 and routed into the recess 16 through the opening 20. The first pulling thread 84 is then routed through the ear 86 of the tensioning spring 18 and subsequently to the reel body 28; to be precise in such a manner that said pulling thread is inserted into the notch 30 of said reel body.

A second pulling thread 88 is routed correspondingly, i.e. towards the underside of the plate 14, through the opening 23, subsequently through the ear 86 of the tensioning spring 18 and then likewise to the notch 30 in the reel body 28.

The two free ends of the two pulling threads 84 and 88 have been connected to form a knot 90.

The pulling threads 84 and 88 routed away from the plate 14 are connected appropriately, depending on the surgical technique applied or on which skin stretching process is to be performed.

When constructing a neovagina, the pulling threads, as described in DE 103 49 953 B1 which was mentioned at the outset, are for example connected to a plastic olive or phantom inserted into the vaginal dimple.

In order to affix and tension the pulling threads, the securing lever 59 is grasped in the raised or pivoted-upwards normal position, the tensioning element 26 is pressed in and turned against the force from the spring 52, with the pulling threads 84 and 88 then being wound onto the reel body 28 and being tensioned accordingly depending on the rotational state.

Figure 4:
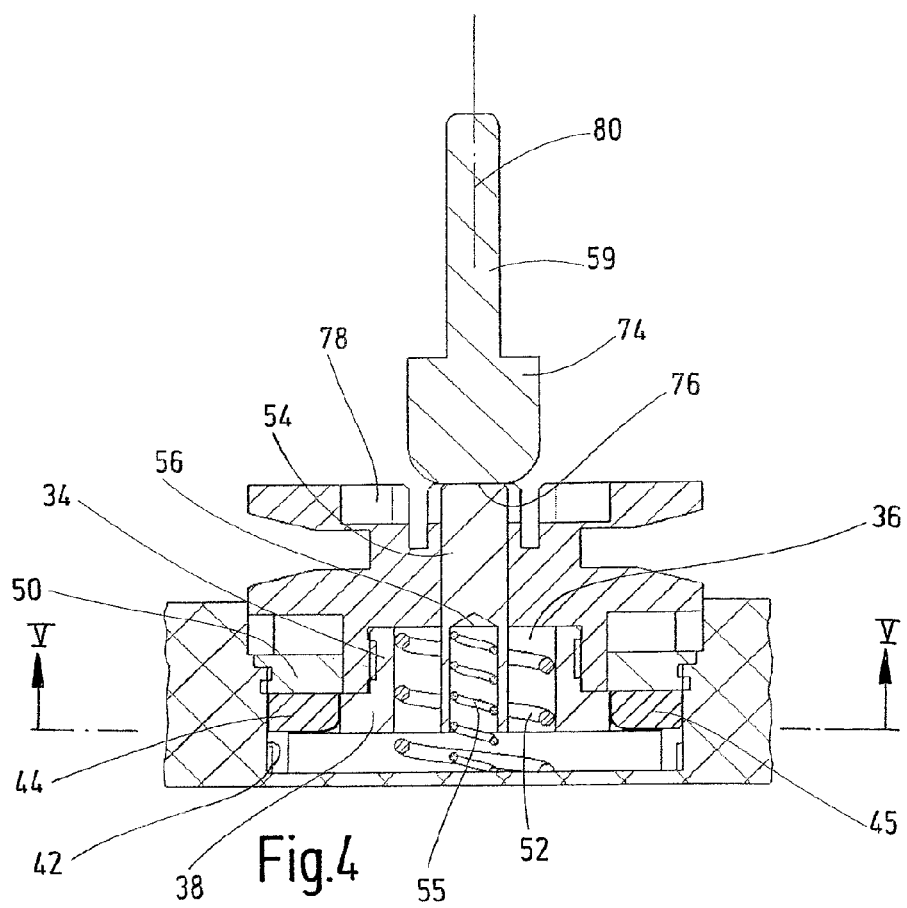
FIG. 4 shows a partial section along the line IV-IV in FIG. 1.

As a result of releasing the securing lever 59 or by reducing the pressing-in force, the first spring 52 presses the reel body 28 upwards (in the illustration of FIG. 6) again, along the longitudinal axis 80, into the normal position illustrated in FIG. 4, in which the latching lock 51 is effective again.

If the device 10 is to be used to perform skin stretching in accordance with EP 2 279 701 A1, the two pulling threads 84 and 88 are subcutaneously routed to a further plate, which is arranged on the opposite side of the lesion to be removed. By tensioning the pulling threads, these two plates are then moved towards one another, the lesion situated therebetween is piled up to form a bead, with the region of skins situated "behind" the plates then being stretched in each case.

It should be mentioned only for the sake of completeness that, during pressing-in, it is also necessary to press against the force from the second spring 55, which is held in the securing pin 54. However, the main function of this second spring 55 is to hold the securing pin 54 respectively resting against the cam 74 of the securing lever 59.

Figure 7:
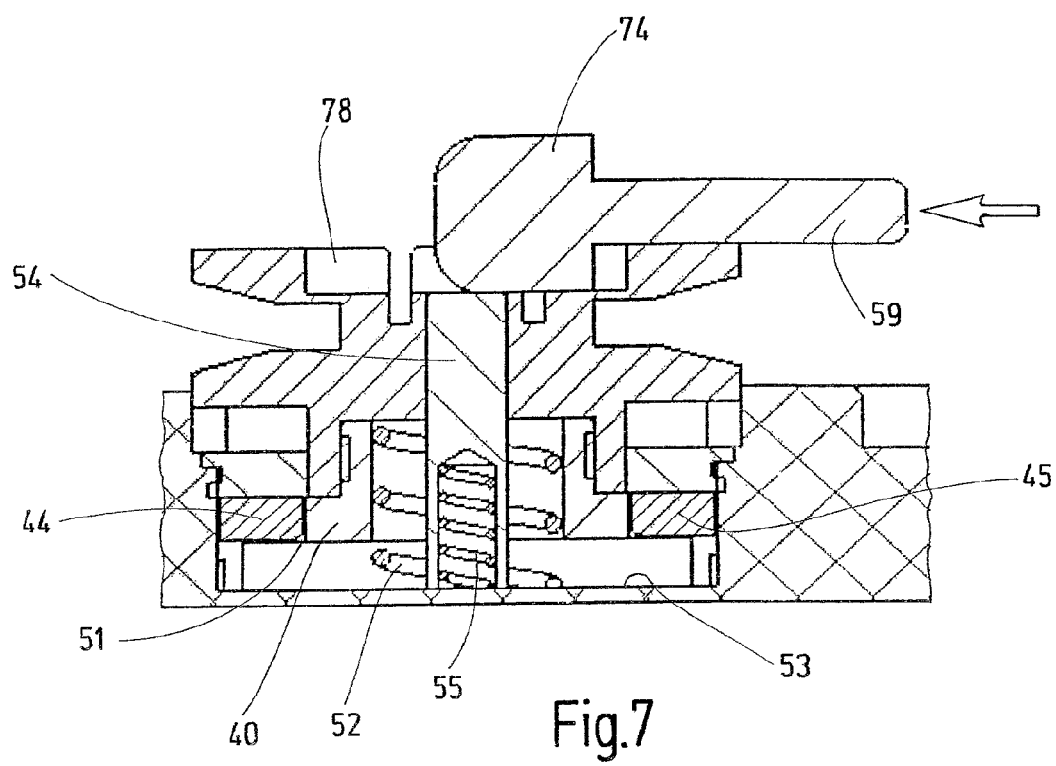
FIG. 7 shows the corresponding section with laterally pivoted down securing lever.

Now, FIG. 7 illustrates a second position of the securing lever 59, namely the laterally pivoted-down or pivoted-over position. This pivoting-over or pivoting-down of the securing lever 69 proceeds from the "normal position" illustrated in FIG. 4. From the transition from FIG. 4 to FIG. 7, it is possible to identify that, when the securing lever 59 is pivoted over, the cam 74 thereof presses the securing pin 54 into the out-out 24 against the force from the second spring 55, right up to cutting against the base 53. Once the securing pin 54 has reached this position illustrated in FIG. 7, it is now no longer possible, for example by pressing on the pivoted-down securing lever 59 in the direction of the axis of rotation 80, to move this assemblage into the cut-out 24 because this movement is blocked by the securing pin 54.

From the sectional illustration FIG. 7 it is possible to identify that the latching lock 51 is in blocking engagement in this state. Even if the outer end of the pivoted-over securing lever 59 were to be grasped and put into a rotational movement, this movement has been blocked by the latching lock 51.

It is possible to identify from the illustration of FIG. 7 that the pivoted-over securing lever 59 projects relatively far beyond the reel body 28 in the lateral direction.

Now, in the case of a person on whom such a device 10 has been affixed, it is not possible to preclude that forces which result from inattentive handling or from pieces of clothing are able to act on the securing lever 59 such that the latter pivot upwards.

Figure 8:
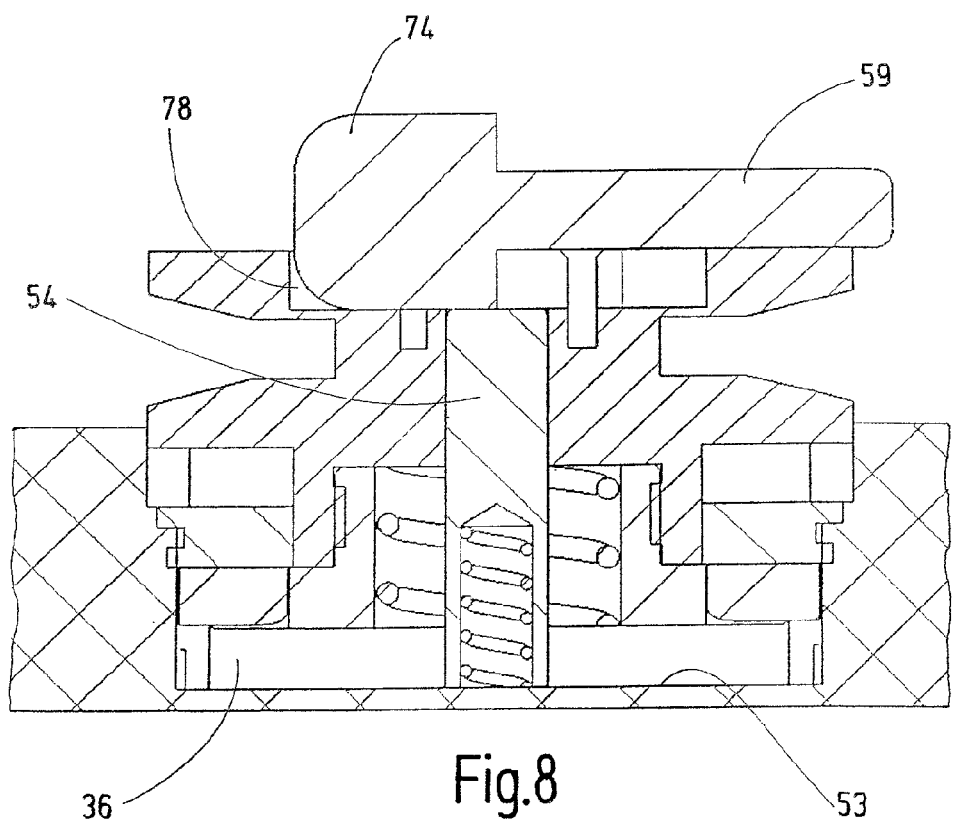
FIG. 8 shows a section corresponding to FIG. 7 after lateral displacement of the pivoted down securing lever.
Figure 9:
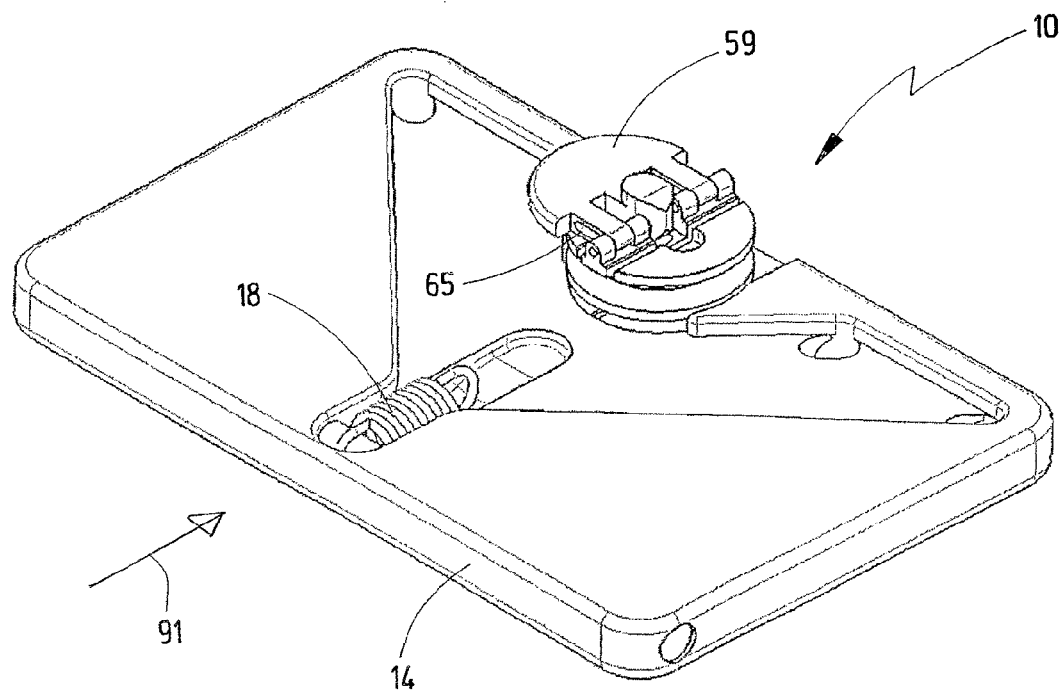
FIG. 9 shows a perspective view of the device from FIG. 1 with the pivoted down securing lever.

Therefore, provision is still additionally made for the securing lever to be able to be displaced laterally from the pivoted-down position illustrated in FIG. 7, with this being illustrated by the transition from FIG. 7 to FIG. 8.

In the further, laterally displaced position of the pivoted-over securing lever 59 illustrated in FIG. 8, the cam 74 of said securing lever still rests on the securing pin 54 such that the securing function against inadvertent pressing-in of the tensioning element 26, and hence inadvertent releasing of the latching lock 51, is still ensured. However, in the position illustrated in FIG. 8, the securing lever 59 can no longer be pivoted upwards.

This will now be explained in more detail in conjunction with FIGS. 9 to 12.

Figure 3:
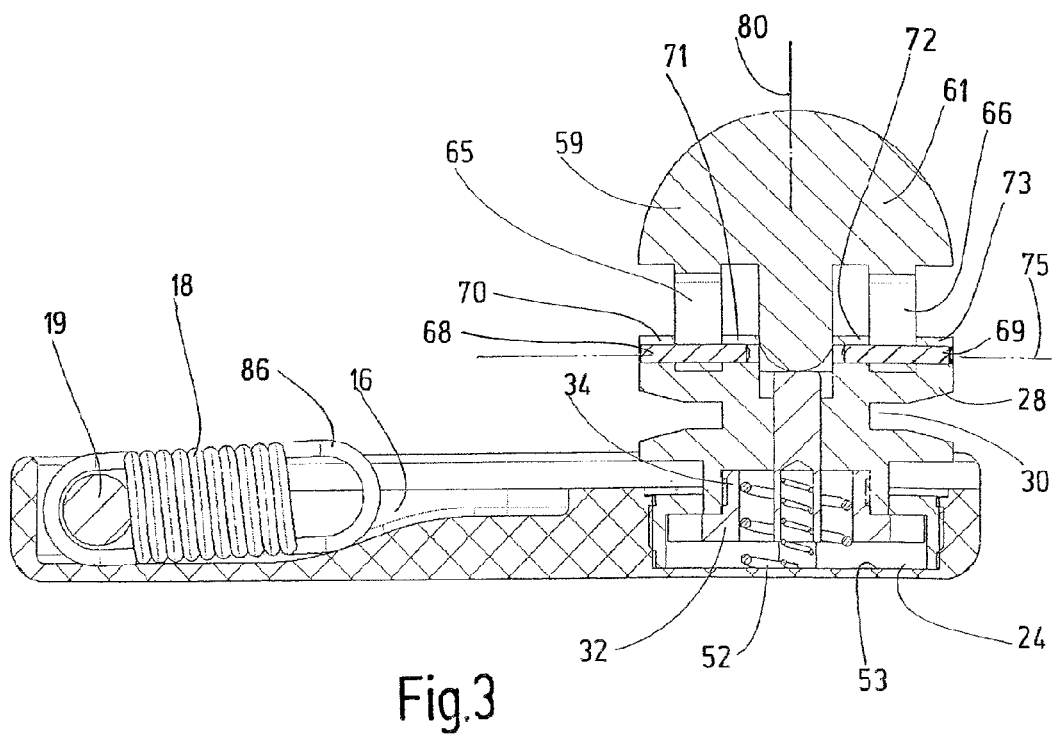
FIG. 3 shows a section along the line in FIG. 1, but without pulling threads.
Figure 10:
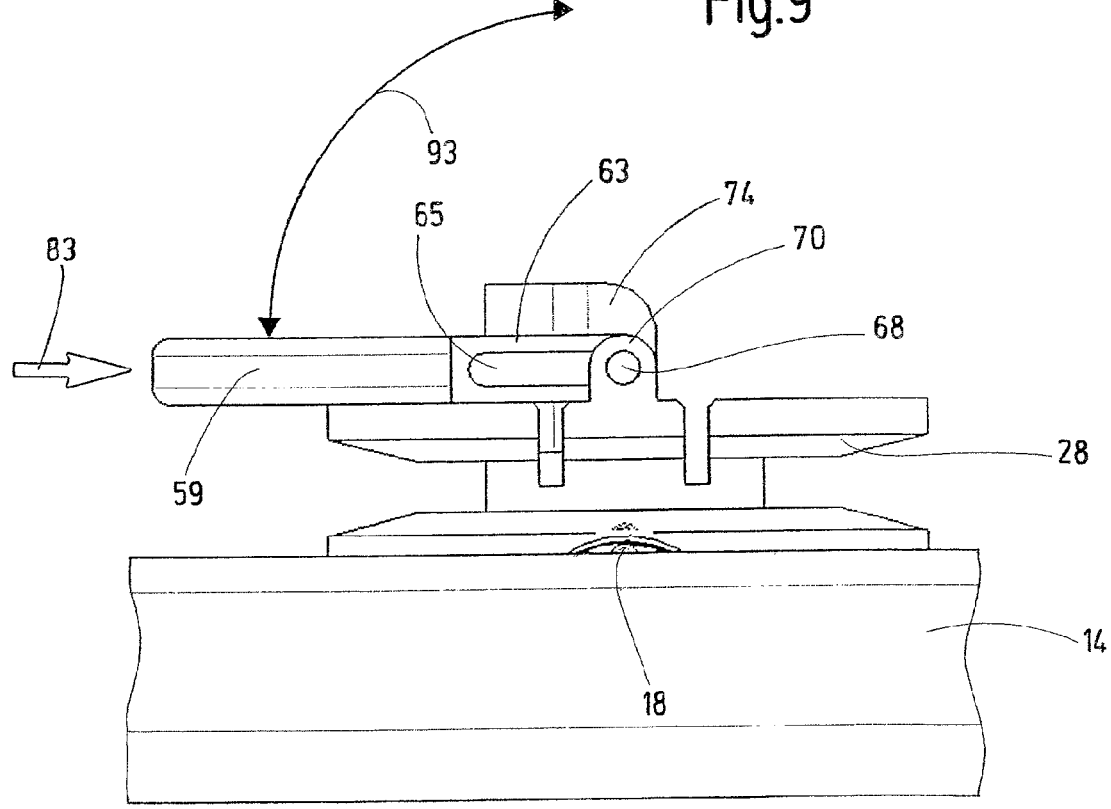
FIG. 10 shows a partial lateral view of the device from FIG. 9 along the arrow 91.

As already explained in conjunction with FIGS. 2 and 3, the two flaps 63 and 64 protrude from the securing lever 59 and the axle pins 68 and 69 are inserted into the slots 65 and 66 of said flaps. In the normal position illustrated in FIGS. 2 and 3, the axle pins 68 and 69 are situated at the "lower" (in this illustration) and of the slots 65 and 66. In this position, as mentioned previously, the swinging, i.e. the raising and pivoting-down of the securing lever 59 is possible, as indicated in FIG. 10 by the arrow 93. If the securing ever 59 is displaced laterally from the position illustrated in FIGS. 9 and 10 into the position illustrated in FIGS. 11 and 12, i.e. along the arrow 83 indicated in FIG. 10, the flaps 63 and 64 are displaced over the axle pins 68 and 69 until the axle pins 68 and 69 butt against the opposite ends of the slots 65 and 66, with this position being illustrated in FIGS. 11 and 12.

Here, the regions of the flaps 63 and 64 reaching beyond the axle pins 68 and 69 rest against the upper side of the reel body 28.

Hence these projecting flaps 63 and 64 block the securing lever 59 from being raised from this further, laterally displaced position of the securing lever 59. As is possible to identify from FIG. 11 in particular, the approximately semicircular areal element 61 of the securing lever 59 lies flush on the upper side of the reel body 28 and no longer projects beyond the latter in a significant manner.

This now brings about the "double" securing. The first securing aspect consists of the tensioning element 26 being blocked from being pressed in when the securing lever 59 is pivoted over, regardless of whether the latter is in the sliding position illustrated in FIG. 7 or 8, and so inadvertent movement and hence release of the latching lock 51 is precluded.

Figure 11:
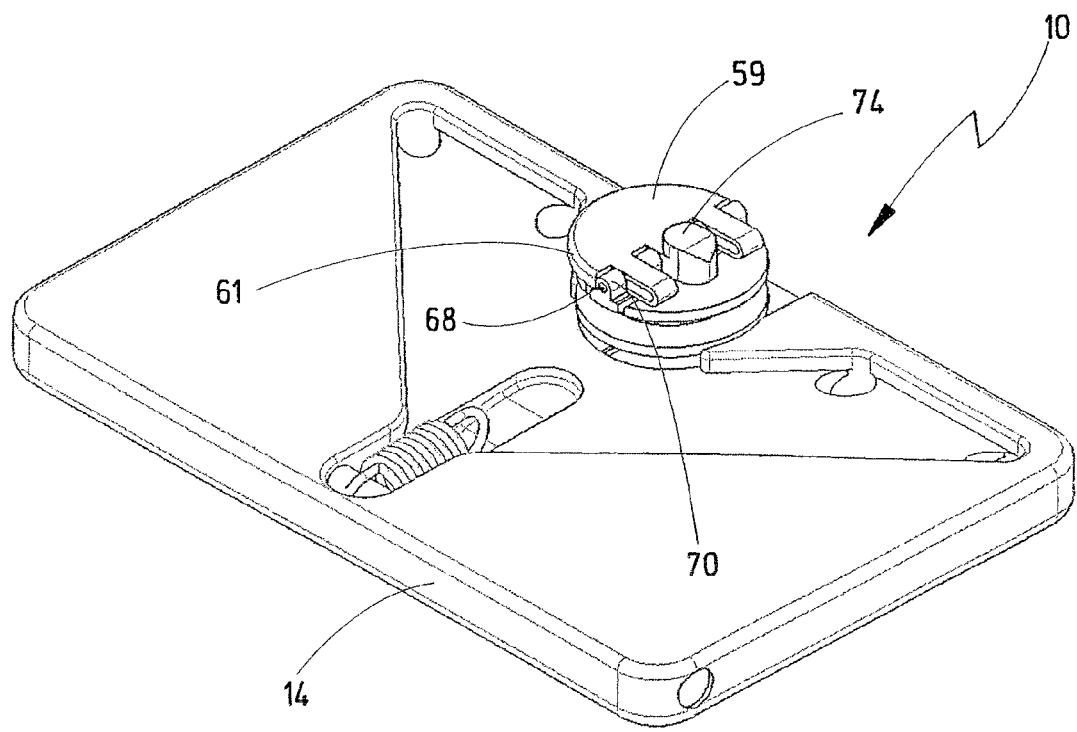
FIG. 11 shows a perspective illustration, comparable to FIG. 9, after lateral displacement of the securing lever
Figure 12:
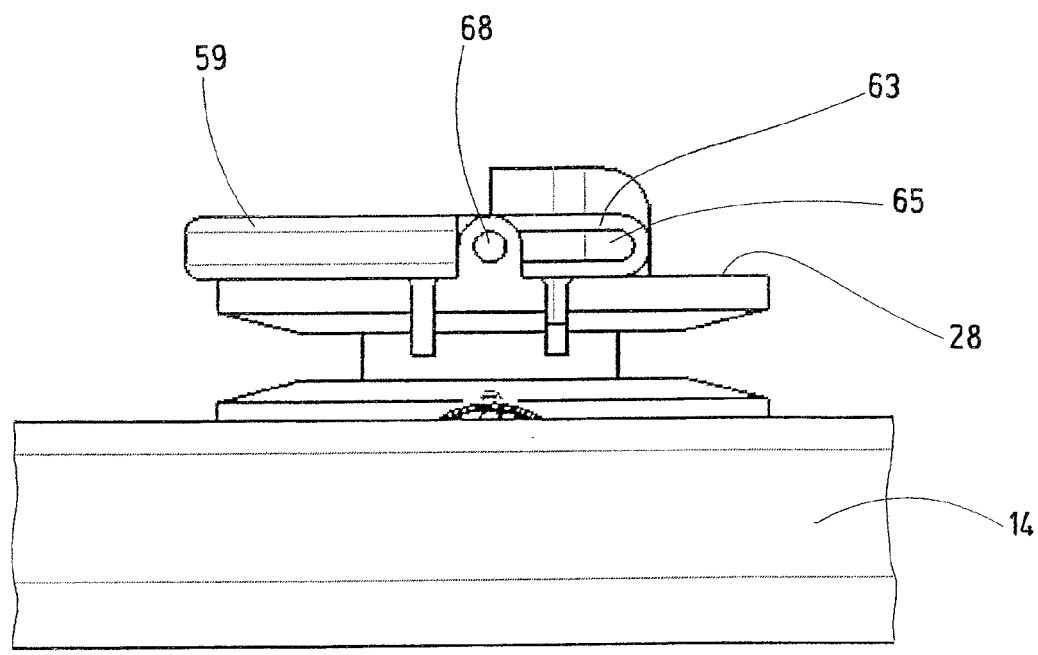
FIG. 12 shows an illustration, comparable to the illustration of FIG. 10, after lateral displacement of the securing lever.

In the lateral displacement state illustrated in FIGS. 11 and 12, the second stage of securing has now been achieved, namely that the pivoted-over securing lever 59 itself is blocked against pivoting upwards.

It is striking, particularly from the illustrations of FIGS. 11 and 12, that the device has no awkwardly shaped protruding components that can become entangled with the clothing of the patient or that constitute starting points by means of which the tensioning element 26 could be inadvertently actuated. It is possible to identify that such a device 10, for example affixed to the chest or the abdominal region, does not constitute a significant handicap, in particular not a handicap that can be identified from the outside either.

In order to actuate the device, the patient must in any case obtain access to the securing lever 59, and so the pieces of clothing must then necessarily be removed. Lateral displacement of the securing lever 59 from the position in FIG. 12 to the one in FIG. 10 provides the prerequisite for the securing lever being able to be pivoted upwards.

This position can be identified firstly by the fact that the securing lever 59 now projects laterally beyond the reel body, or this can be identified by virtue of the fact that said securing lever can no longer be displaced in this direction because this is blocked by the abutment of the axle pins 68 and 69 in the slots 65 and 66. Now it is possible, as illustrated in FIG. 10, to pivot the securing lever 59 upwards.

By pressing in and turning, as illustrated in FIG. 6, it is possible to initially release the latching lock 51 and turn the reel body 28, as a result of which the pulling threads 84 and 88 are then successively wound up and correspondingly tensioned. Once a sufficient tension has been achieved (the pulling pain from the pulling threads can be felt), the patient releases the tensioning element 26 or reduces the pressing-in force such that the tensioning element is pushed upwards again into the blocking position by the force from the first spring 52. Then the patient pivots the securing lever 59 again, displaces the latter laterally and awaits the next tensioning procedure.

What is claimed is:

1. A device for stretching skin, comprising
   a plate-shaped main body;
   a tensioning element arranged on said main body, said tensioning element being rotatable about an axis of rotation, such that a pulling thread affixed on said tensioning element is configured to be wound up on said tensioning element and tensioned;
   a latching lock for fixing said rotatable tensioning element and preventing inadvertent release of said tensioning element; and
   a securing lever arranged on said tensioning element, said securing lever being movable both around said axis of rotation and in a direction of said axis of rotation;
   wherein said tensioning element is able to be moved in the direction of said axis of rotation against a force of a spring which causes said latching lock to be removed from a latching position,
   wherein when said tensioning element is released, said latching lock can be returned to said latching position as a result of said force from said spring, and
   wherein said latching lock and a movement of said tensioning element can be actioned by said securing lever at a same time,
   wherein said securing lever is configured to be actioned in
      a first position where said securing lever is raised from said tensioning element and is not secured,
      a second pivoted down position where said securing lever blocks a movement of said tensioning element in said direction of said axis of rotation, and
      a third position which prevents said securing lever from raising upwards, where said securing lever can, from said second pivoted down position, be laterally displaced relative to said axis of rotation into said third position.

2. The device of claim 1, wherein said securing lever can be pivoted down about a lever axis which runs perpendicularly to said axis of rotation of said tensioning element.

3. The device of claim 2, wherein said securing lever rests on a securing pin, extending along said axis of rotation of said tensioning element, via a cam, said securing pin allowing a movement of said tensioning element along said axis of rotation of said tensioning element in a first, pivoted upwards position of said securing lever but blocking said movement in said second pivoted down position.

4. The device of claim 3, wherein said cam has a rounded cam surface facing said securing pin, said cam surface actioning as an axial displacement of said securing pin along said axis of rotation when said securing lever is pivoted down or upwards.

5. The device of claim 1, wherein said securing lever has at least one slot, in which at least one axle pin extending along a lever axis is held, and wherein, in said second pivoted down position of said securing lever, the securing lever can be swung about said at least one axle pin but a swinging movement is prevented in said third position of said securing lever, since said at least one axle pin being laterally disposed in said at least one slot.

6. The device of claim 1, wherein said tensioning element is held in a cut-out in said main body, and wherein said axis of rotation stands up from said main body, and wherein said tensioning element can be moved towards said main body against said force from said spring.

7. The device of claim 6, wherein said latching lock has at least one latch protruding into said cut-out in said main body, said at least one latch, is in a blocking engagement with a toothed wheel of said tensioning element in said latching position.

8. The device of claim 7, wherein said at least one latch is chamfered at flanks thereof.

9. The device of claim 7, wherein teeth of said toothed wheel are chamfered at flanks thereof.

10. The device of claim 1, wherein said tensioning element has a reel body, onto which said pulling thread can be wound, and wherein said securing lever is assembled on one end of said reel body facing away from said main body.

11. The device of claim 10, wherein said securing lever is a plane element, which comes to a rest on said end of said reel body in said second pivoted down position.

12. The device of claim 11, wherein two flaps protrude from said plane element, into which flaps slots have been cut out, and wherein one axle pin extending along a lever axis is respectively held in said flaps slots.

13. The device of claim 12, wherein said flaps project from one side of said lever axis and rest against said reel body when said securing lever is pivoted down and laterally displaced, as a result of which said securing lever is prevented from being raised upwards.

14. The device of claim 13, wherein said flaps extend away from said plane element in a plane of the latter.

* * * * *